United States Patent [19]

Kao et al.

[11] Patent Number: 5,079,267
[45] Date of Patent: Jan. 7, 1992

[54] METHANOL PRODUCTION

[75] Inventors: Richard L. Kao, Naperville; Sarabjit S. Randhava; Surjit S. Randhava, both of Evanston, all of Ill.

[73] Assignee: Xytel Technologies Partnership, Mt. Prospect, Ill.

[21] Appl. No.: 409,417

[22] Filed: Sep. 16, 1989

[51] Int. Cl.⁵ .............................................. C07C 27/06
[52] U.S. Cl. .................................. 518/704; 518/705; 518/713; 518/728
[58] Field of Search ................ 518/704, 705, 713, 728

[56] References Cited

U.S. PATENT DOCUMENTS

| | | |
|---|---|---|
| 3,501,516 | 11/1968 | Parrish . |
| 3,962,300 | 6/1976 | Hiller et al. . |
| 3,993,457 | 11/1976 | Cahn et al. . |
| 4,013,454 | 3/1977 | Jordan . |
| 4,048,250 | 9/1977 | Garwood et al. . |
| 4,122,110 | 10/1978 | Sugier et al. . |
| 4,219,492 | 8/1980 | Konoki et al. ...................... 518/704 |
| 4,271,086 | 6/1981 | Supp et al. .......................... 252/373 |
| 4,348,487 | 9/1982 | Goldstein et al. .................. 518/713 |
| 4,559,207 | 12/1985 | Hiller et al. ........................ 518/713 |
| 4,650,814 | 3/1987 | Keller .................................. 518/705 |
| 4,910,228 | 3/1990 | Lywood ............................. 518/704 |
| 5,477,206 | 1/1983 | Pinto .................................. 518/704 |

FOREIGN PATENT DOCUMENTS 1159035 7/1969 United Kingdom .
2142331 1/1985 United Kingdom .

OTHER PUBLICATIONS

Monnier, J. R., Apai, G., and Hanrahan, M. J., "Effect of $CO_2$ on the Conversion of $H_2/CO$ to Methanol Over Copper-Chromia Catalysts", Journal of Catalysis, 88, pp. 523-525 (1984).

Monnier, J. R., and Apai, G., "Effect of Oxidation States on the Syngas Activity of Transition-Metal Oxide Catalysts", American Chemical Society, 191st National Meeting, Apr. 13-18, 1986.

Primary Examiner—Howard T. Mars
Attorney, Agent, or Firm—Speckman & Pauley

[57] ABSTRACT

A process for production of methanol from process gas produced by steam reforming hydrocarbon feedstocks in a tube type reformer followed by removing substantially all $CO_2$ and $H_2O$ from the process gas, adjusting the $H_2/CO$ molar ratio to about 2 when necessary, and feeding the adjusted process gas to a methanol synthesis reactor contacting a methanol forming catalyst not requiring $CO_2$ activation at about 200° to about 300° C. to produce product gas comprising methanol, and recovering liquid methanol having purity greater than about 99.85% pure by cooling the product gas to a temperature below the boiling point of methanol and separating the liquid methanol from gaseous components of the product gas. In a preferred embodiment, process gas of $H_2/CO$ molar ratio of about 2.0 to about 2.5 is passed through an annular thermal exchange volume between a center plug and an inner tube followed by passing the gas in contact with a catalyst in a catalyst bed between the inner tube and an outer tube of a double tube reactor assembly promoting the direct reaction of $H_2$ and CO to product methanol. An improved double tube reactor having a plurality of inner and outer tube assemblies each of the assemblies having a reaction annular volume between the inner tube and outer tube and a closed center plug within the inner tube forming an annular thermal exchange volume between the center plug and the inner tube.

47 Claims, 2 Drawing Sheets

METHANOL PRODUCTION

BACKGROUND OF THE INVENTION

1. Field of the Invention

This invention relates to a low pressure, low temperature process for production of high purity methanol from near stoichiometric ratios of hydrogen and carbon monoxide and an improved double tube reactor therefor.

2. Description of the Prior Art

Until a high pressure/high temperature methanol synthesis technology was developed by BASF in Germany in 1923, distillation of wood was the only commercially significant method to produce methanol. The high pressure/high temperature technology employed a synthetic route using pressurized gas mixtures of $H_2$, CO, $CO_2$ and $CH_4$ in the presence of Zn-Cr based catalysts. The pressurized gas mixtures for methanol synthesis were derived from mixing steam with gaseous, liquid or solid hydrocarbon feedstocks, and preheating to 425° to 550° C. before feeding to a reformer. Very high pressures, typically 300 to 350 atmospheres, were applied in order to obtain a reasonable conversion at the high operating temperatures of the Zn-Cr based catalysts (320° to 380° C.) where the methanol synthesis equilibrium constraints are poor.

In the 1960's, highly active and durable copper-zinc oxide based catalysts were developed for methanol synthesis. These catalysts were so active that the methanol synthesis process could operate at much lower temperatures, 200° to 300° C., than the prior processes and permitted the use of lower operating pressures, 50 to 150 atmospheres. By the late 1970's, most of the methanol synthesis plants in the United States used low pressure technology due to the advantages of lower compression costs, reduced byproduct formation, longer catalyst life, and lower capital costs. The major differences among these low pressure methanol synthesis processes were in the methanol reactor designs used to remove the heat generated by the highly exothermic methanol synthesis reaction and the reformer configurations: one-stage or two-stage reforming. All of the modern low pressure technologies have required a large compressor to bring the process gas to the methanol reactor operating pressure and a step to remove the compressor oil before the methanol synthesis loop. Also, the raw methanol produced from these processes contained approximately 25 mole % water and impurities such as dimethyl ether and higher alcohols. Therefore, a methanol purification step of stripping columns, distillation columns, and the like was needed in order to achieve the required methanol purity.

Several United States patents teach the reaction of $H_2$ plus CO to form methanol. U.S. Pat. No. 4,122,110 teaches the reaction of $H_2$ and CO in the presence of a catalyst having at least four metallic components to form linear saturated primary alcohols, the selectivity of $C_2$ or more often being higher than 70% by weight. Several patents teach removal of $CO_2$ from process gas obtained from a hydrocarbon/steam reforming process prior to reaction of $H_2$ and CO in a methanol forming reactor: British patent 1,159,035 teaching $CO_2$ maybe removed completely from the synthesis gas, but part of the removed $CO_2$ is added to the feed to the methanol reactor using a catalyst containing CuO and ZnO and at least one other difficultly reducible Group II to IV metal oxide; U.S. Pat. No. 4,348,487 teaching production of methanol by catalytic coal gasification wherein $CO_2$ is removed from the process gas and then reintroduced back into the methanol synthesis zone feed in order to activate the methanol synthesis catalyst; U.S. Pat. No. 3,962,300 teaching a process for producing methanol using a partial oxidation treatment followed by methanol formation by contacting with a copper-containing catalyst which is indirectly cooled with water boiling under superatmospheric pressure resulting in the production of high pressure steam which is expanded by generating power to produce compression energy for the gases to be compressed in the process, thereby recognizing the problem of compression energy in the methanol production process; and U.S. Pat. No. 4,013,454 teaching partial removal of $CO_2$ in a simultaneous production of methanol or ammonia and again recognizing the problem of $CO_2$ and compression energy in the methanol synthesis process.

A number of patents relating to methanol synthesis recognize that $CO_2$ and $H_2O$ are in the product methanol and must be removed by downstream processes to obtain high purity methanol: U.S. Pat. Nos. 3,501,516; 3,993,457; 4,048,250; and United Kingdom patent application 2142331A.

The use of $Cu-Cr_2O_3$ as a selective catalyst for methanol production without the requirement of $CO_2$ for catalyst activity promotion has been recognized in Monnier, J. R., Apai, G., and Hanrahan, M. J., "Effect of $CO_2$ on the Conversion of $H_2$/CO to Methanol over Copper-Chromia Catalysts", Journal of Catalysis, 88, pg. 523-525 (1984). The characterization and catalytic activity for methanol formation using promoted Cu-Cr oxide catalysts is taught by J. Monnier and G. Apai, "Effect of Oxidation States on the Syngas Activity of Transition Metal Oxide Catalysts", American Chemical Society, 191st National Meeting, April 13-18, 1986.

SUMMARY OF THE INVENTION

This invention relates to low pressure, low temperature catalytic production of methanol from near stoichiometric ratios of hydrogen and carbon monoxide. The process may use hydrocarbon feedstock for steam reforming in a reformer furnace using a pressurized burner to provide higher reformer temperatures. Burner pressure is maintained at about 100 to about 300 psi to result in reformer reaction temperature of about 850° to about 1010° C. to form process gas comprising principally $H_2$, CO, $CH_4$, $CO_2$ and $H_2O$. Higher reforming temperatures produce less methane which reduces the gas volume in the front end of the process and lowers the purge gas rate from the methanol synthesis loop. This allows the application of higher pressure in the reformer tube and makes possible great reduction and elimination of the conventional costly process gas compressor prior to methanol synthesis. The process gas produced by reforming of hydrocarbon feedstock is cooled followed by $CO_2$ and $H_2O$ removal. The $CO_2$ content of the process gas is reduced to less than about 500 ppm $CO_2$ and the $H_2O$ content to less than about 50 ppm $H_2O$. Recovered $CO_2$ is recycled to the reformer and will decrease the $H_2$/CO molar ratio in the process gas from natural gas feedstock from about 5 to about 3 when a steam/C molar ratio of about 3 is used in the feedstock. This process provides very high carbon utilization. The $H_2$/CO molar ratio is adjusted to about 2 and slightly greater, the desired stoichiometric ratio for feed to a methanol synthesis reactor. The methanol synthesis reactor uses a methanol forming catalyst not requiring $CO_2$ activation. Preferred catalysts include alkali and alkaline earth promoted copper-chromia catalysts. Since the catalyst does not require $CO_2$ activation, the absence of $CO_2$ permits reduction and elimination of costly methanol purification, such as strippers and distillation columns. According to this invention, the reacted gas flows to a cooler/condenser and separator. The liquid product from the separator passes through a second separator where the pressure is reduced to release the dissolved gases for reformer fuel. The liquid methanol produced will have 99.85% plus purity. A small portion of the gas released in the first separator is purged in order to maintain a suitable level of inert ($CH_4$) gas in the synthesis loop. The major portion of this gas is mixed with the make-up synthesis gas and recycled to the inlet of the methanol reactor.

In one preferred embodiment, the process of this invention passes process gas comprising $H_2$ and CO in molar ratio $H_2/CO$ of about 2.0 to about 2.5 in a single pass fashion through an annular thermal exchange volume between a center plug and an inner tube of a double tube methanol synthesis reactor followed by passing the heated gas through an annular catalyst bed between the inner tube and the outer tube of the double tube reactor in contact with a catalyst for promotion of reaction of the $H_2$ and CO to product comprising principally methanol. An improved double tube reactor has a plurality of inner tube and outer tube assemblies, each of which assemblies have an annular catalyst bed and reaction volume between the inner tube and the outer tube and a closed center plug within the inner tube forming an annular thermal exchange volume between the center plug and the inner tube. It is preferred that the center plug have a diameter at least 75% the inner diameter of the inner tube and be pointed on the end facing toward the entry end of the inner tube. This reactor design features high one-pass conversion and high heat recovery.

It is an object of this invention to provide a process and apparatus for production of methanol providing significant reduction of energy consumption and capital investment.

It is another object of this invention to provide high conversion to methanol without the need of a process gas compressor.

It is yet another object of this invention to provide a process for methanol production wherein removal of $CO_2$ and $H_2O$ from the methanol synthesis reactor feed stream eliminates the need for methanol purification, the methanol synthesis reactor providing product gas from which liquid methanol having purity greater than about 99.85% pure may be recovered solely by water cooling the product gas to a temperature below the boiling point of methanol and separating the liquid methanol from gaseous components.

Yet another object of this invention is to provide a methanol synthesis reactor design which results in more favorable temperature profiles for methanol formation and steadier and more reliable operation.

BRIEF DESCRIPTION OF THE DRAWING

The above and other advantages of this invention will become apparent as this description proceeds taken in conjunction with the drawings wherein.

DESCRIPTION OF PREFERRED EMBODIMENTS

Figure 1:
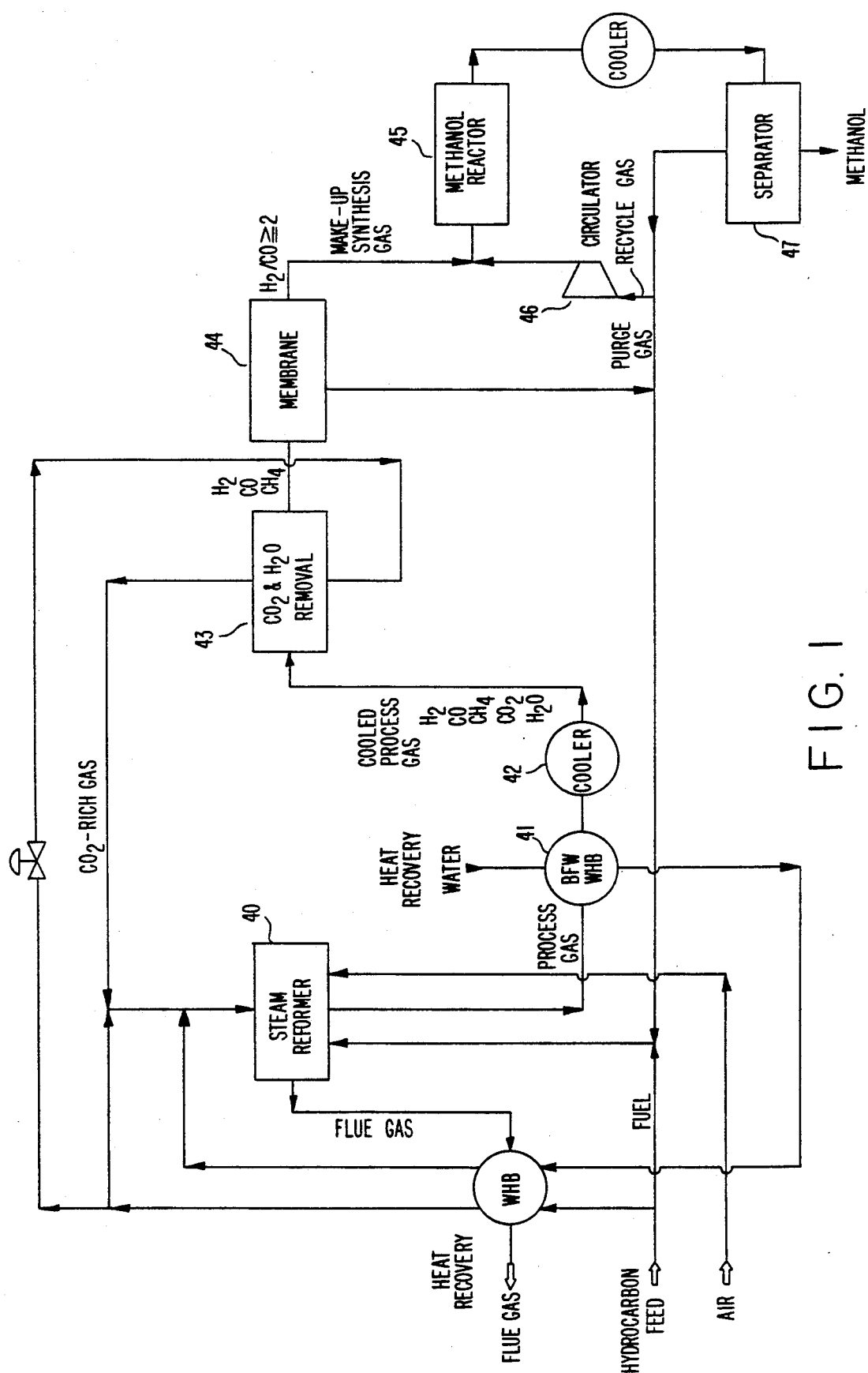
FIG. 1 is a simplified schematic process flow sheet of the process of this invention.

Referring to FIG. 1, the overall process may be divided into four principal sections: reforming; process gas $CO_2$ and $H_2O$ removal; $H_2/CO$ stoichiometry adjustment; and methanol synthesis loop.

As shown in FIG. 1, hydrocarbon feed, steam and air are fed to steam reformer 40. One method of overcoming problems of stress-rupture failures of the catalyst tubes due to high temperature/high pressure operation is to use a pressurized burner in the reformer according to this invention, burner pressures suitably maintained at about 100 to 300 psi and preferably about 150 to 200 psi to provide higher reformer reaction temperatures of about 850° to about 1010° C. and preferably about 950° to about 1010° C. For example, a 100 psi increase in burner pressure can increase the temperature of a reformer tube from 954° C. to about 982° C. Reformer tubes which will withstand the additional temperature must be used in the steam reformer 40. Suitable desulfurized hydrocarbon feeds to the steam reformer according to this invention include gaseous, liquid, and solid hydrocarbon feedstocks, and mixtures thereof. For example, natural gas may be used as feedstock, hydrocarbon oils may be used as feedstock, and coal or shale may be used as feedstock, and mixtures of such feedstocks may also be used, as is well known in steam reforming techniques. Operation of the steam reformer of this invention at higher temperatures than conventional steam reformers results in lower methane in the process gas and reduces the methane purge rate from the methanol synthesis loop and also allows the application of higher pressure in the reformer tube. Process gas, comprising principally $H_2$, CO, $CH_4$, $CO_2$ and $H_2O$ passes through waste heat boiler 41 where high pressure seam is produced. The remaining heat is utilized to the maximum extent as a BFW preheat (41). The final cooling and condensation of extra steam content in the process gas are done by air and water thermal exchange in cooler 42, cooling the process gas to about 43° C. While the process of this invention preferably utilizes process gas obtained by steam reforming of hydrocarbon feedstocks, similar process gas produced by other processes, such as partial oxidation, may also be used.

Carbon dioxide and $H_2O$ removal from the cooled process gas may be achieved by various $CO_2$ and $H_2O$ removal means 43. One desirable method is by pressure swing absorption using molecular sieves. The pressure swing absorption product gas would contain less than about 10 ppm $H_2O$ and less than about 500 ppm, preferably less than about 100 ppm, $CO_2$. The pressure swing absorption molecular sieve process is advantageous since it requires virtually no utilities and no operating attention, operates at ambient temperature, fully automated, with no external regenerant gas, and may be shut down and started up quickly with very little attention. The recovered $CO_2$ stream contains about 15% of the feed $H_2$, 30% of the feed CO and 40% of the feed $CH_4$ which may be recycled back to the steam reformer. Another system for $CO_2$ and $H_2O$ removal is to use an inhibited amine system to scrub the $CO_2$ followed by a thermally regenerated molecular sieve gas dryer wherein the cooled process gas enters the bottom of a $CO_2$ absorber and flows up through either packed beds or trays countercurrent to an aqueous solution of alkanolamine, such as monoethanolamine and diethanolamine, wherein $CO_2$ may be removed from the process gas to less than 100 ppm. The $CO_2$-rich spent solution is pumped from the bottom of the absorber to a lean/rich heat exchanger where it is heated to above 100° C. by a hot lean alkanolamine solution. Then the alkanolamine solution is fed to the top of a stripper where the absorbed $CO_2$ is stripped from the descending spent solution by a rinsing hot stream of steam which is generated by a reformer waste heat boiler. The steam and recovered $CO_2$ are recycled to the reformer feed while the regenerated or lean alkanolamine solution flows to the lean/rich heat exchanger before it is pumped to the top of the absorber for completion of the purification cycle. The purified gas passes through a molecular sieve gas dryer to remove the moisture and part of the remaining $CO_2$. The dryer may comprise dual molecular sieve chambers, one of which may be on a process line and one of which may be regenerated by a hot stream of pressurized $CH_4$. The alkanolamine stripping has the advantage of about a 99% recovery of $H_2$ and $CO$ while producing a product gas with less than about 100 ppm $CO_2$. However, the alkanolamine stripping process has some disadvantages when compared to the pressure swing absorption molecular sieve process in that it requires more operating attention and has heat input and cooling water requirements in addition to the molecular sieve gas dryer. Another process for removal of $CO_2$ and $H_2O$ is the use of physical solvents such as the Selexol system which uses an absorber for the process gas $CO_2$ and $H_2O$ removal simultaneously and a stripper for regeneration of the spent solution first by stripping, followed by flashing. The advantage of this system is that $CO_2$ can be recovered by stripping with a hot stream of pressurized $CH_4$ or steam, thus eliminating the need for $CO_2$ recycle compressor. A major disadvantage of this system is that external cooling is required. Any of the above $CO_2$ and $H_2O$ removal systems may be used in the process of this invention and the choice is dependent upon optimizing the design for individual applications, depending upon available utilities.

$H_2/CO$ stoichiometry adjustment may be effected by any suitable adjustment means shown in FIG. 1 as 44, such as a membrane unit. It is desired that the feed gas to methanol synthesis reactor 45 has an $H_2/CO$ molar ratio of about 2.0 to about 2.5, preferably about 2.0 to about 2.2. The molar ratio of $H_2$ to $CO$ in the process gas depends upon the hydrocarbon feedstock used. For example, when naphtha is used as the reformer feedstock the $H_2/CO$ molar ratio will be 2, while when natural gas is used the ratio will be about 5. When natural gas and recovered $CO_2$ and $H_2O$ are used as reformer feedstock, the $H_2/CO$ ratio is about 3. As excess $H_2$ accumulates in the methanol synthesis loop, a high purge gas rate is required, the purge stream taking along whatever amount of $CO$ corresponds to the composition in the recycle. It is more economical to remove the excess $H_2$ by a membrane unit before the makeup synthesis gas enters the methanol synthesis loop. Thus a lower recycle ratio is required to accommodate the trace amount of inerts, which results in smaller sized equipment and lower power consumption for the recycle circulator 46.

In prior art methanol synthesis reactors the following reactions have occurred:

$$CO + 2H_2 \rightarrow CH_3OH \tag{1}$$

$$CO_2 + 3H_2 \rightarrow CH_3OH + H_2O \tag{2}$$

$$2CO + 4H_2 \rightarrow CH_3OCH_3 + H_2O \tag{3}$$

$$CO + 3H_2 \rightarrow CH_4 + H_2O \tag{4}$$

$$nCO + 2nH_2 \rightarrow C_nH_{(2n+1)}OH + (n-1)H_2O \quad n>1 \tag{5}$$

According to the process of this invention, when $CO_2$ is not present in the methanol synthesis reactor feed, reaction 2, a major source of water production, does not occur. In the process of this invention using highly methanol selective alkali and alkaline earth promoted copper-chromia catalysts, the side reaction of equation (4) is not present. Since the catalysts used in this invention are low pressure catalysts, the amount of impurities, such as dimethyl ether, higher alcohols, and carbonyl compounds in the methanol are also reduced significantly. Equations (3) and (5) represent side reactions for low pressure methanol processes and we have found the total amount of impurities in the liquid methanol produced in the synthesis loop is normally below about 1000 ppm, therefore, producing a very high purity methanol without the conventional requirement of methanol purification by stripper and distillation columns. The reaction of equation (1) is clearly the predominant reaction of the process of this invention, not producing $H_2O$.

Figure 2:
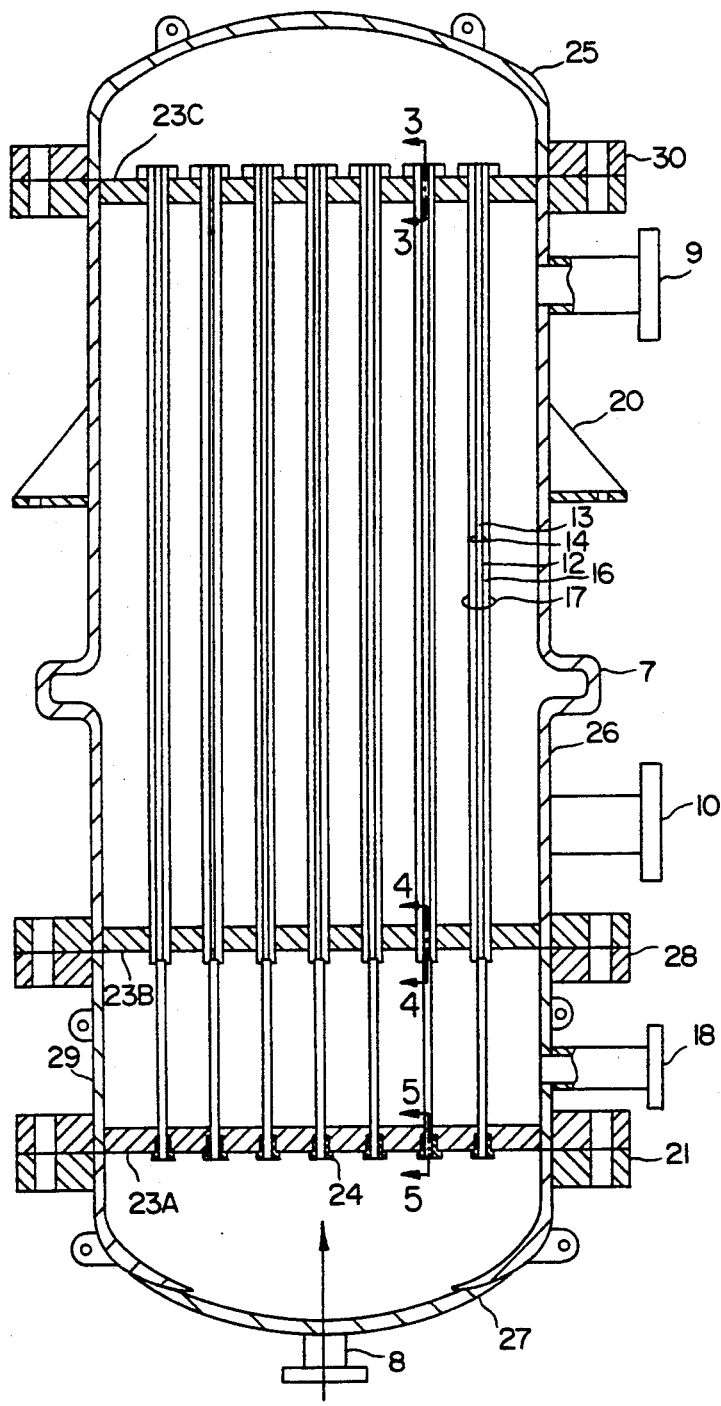
FIG. 2 is a side cross-sectional view of a methanol synthesis reactor suitable for use in this invention.
Figure 4:
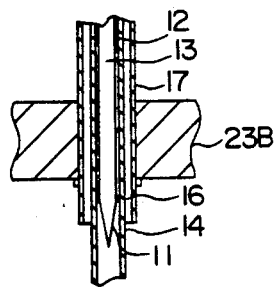
FIG. 4 is an enlarged sectional view of the section shown as 4—4 in FIG. 2.

As shown in FIG. 1, the $CO_2$ and $H_2O$ free process gas having an $H_2/CO$ molar ratio of 2 or slightly greater is mixed with recycle gas from circulator 46 before entering methanol synthesis reactor 45. One suitable methanol synthesis reactor 45 is shown in FIG. 2. The feed process gas to the methanol synthesis reactor enters through inlet conduit 8 in bottom dome 27 of the reactor to enter annular thermal exchange volume 12 between center plugs 13 and inner tubes 14. This may be best seen in FIG. 4 showing center plugs 13 with pointed ends 11 facing the inlet end of inner tubes 14. Between inner tube 14 and outer tube 17 is annular catalyst bed 16. Annular thermal exchange volume 12 between center plug 13 and inner tube 14 and the space outside the outer tube 17 provide superior heat transfer for the catalyst bed 16 and result in good temperature profiles in the catalyst bed 16 for steady-state operation. The process feed gas is preheated by passage through annular thermal exchange volume 12 by reaction heat generated in catalyst beds in annular catalyst volume 16. The preheated process gas enters the volume of upper dome 25 and then passes through annular catalyst beds 16 flowing downward between inner tube 14 and outer tube 17 exiting at methanol gas outlet 18. It is preferred that the center plugs 13 have a diameter at least 75% the inner diameter of the inner tubes 14. Annular catalyst beds 16 are cooled externally by pressurized boiler water entering at inlet 9 and exiting at outlet 10 and internally by process gas passing through the annular thermal exchange volumes 12 between inner tubes 14 and center plugs 13. This provides both radial and vertical temperature profiles in the catalyst beds, a lower temperature at the bottom of the catalyst bed with gradual increase in temperature toward the top which is favorable in terms of methanol formation. The methanol synthesis reactor of this invention provides favorable temperature control, as compared with conventional methanol reactors which may be classified in terms of removal of reaction heat, as adiabatic quench type, interbed cooling type, tubular type, water tube cooling type, and double tube type, all of which tend to have excessive temperatures in the catalyst beds which ages the catalyst and reduces its catalytic activity.

We have found that methanol synthesis reactor temperatures of about 200° to about 300° C. and pressures of about 500 to about 800 psi according to the process of this invention provide liquid methanol having purity greater than about 99.85% pure by cooling the product gas to a temperature below the boiling point of methanol and separating the liquid methanol from gaseous components of the product gas which may then be recycled.

Figure 3:
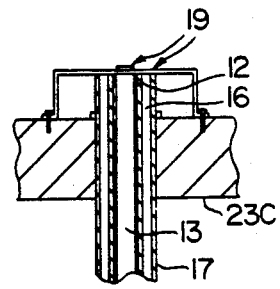
FIG. 3 is an enlarged sectional view of the section shown as 3—3 in FIG. 2.
Figure 5:
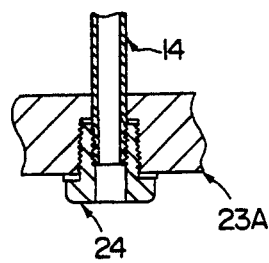
FIG. 5 is an enlarged sectional view of the section shown as 5—5 in FIG. 2.
Figure 6:
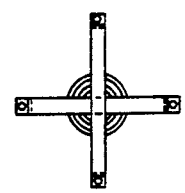
FIG. 6 is a top view of the portion shown in FIG. 3.

In the embodiment shown, the reactor vessel of this invention may be installed vertically, four lug supports 20 holding the entire weight of the vessel. The reactor shown in FIG. 2 provides for simple charge and discharge of the catalyst. Lower dome 27 may be removed from vessel 26 by removing bolts from bottom flange 21, dropping lower dome 27. Lower tube plate 23A is now exposed, and as best seen in FIG. 5, end plugs 24 may be unscrewed from the face of lower tube plate 23A and inner tubes 14 pulled from vessel 26. In a similar manner, lower vessel body 29 may be removed from vessel 26 by removing bolts of flange 28 exposing the open ends of outer tubes 17 from which the catalysts may be readily discharged. As best seen in FIGS. 3 and 4, outer tube 17 is fixed to central tube plate 23B and upper tube plate 23C. As best seen in FIG. 3, center plug 13 is fixed to upper tube plate 23C by bracket 19 which provides opening to annular thermal exchange volume 12 and annular catalyst bed volume 16. To reassemble, reactor lower vessel body 29 is rebolted to vessel 26 by flange 28. Using center plugs 13 as guides, inner tubes 14 are inserted back into outer tubes 17 and end plugs 24 are reinstalled in lower tube plate 23A. Once tightened, inner tubes 14 are supported and fixed by lower tube plate 23A and lower dome 27 is refastened to vessel 26 by bolting through flange 21. Upper dome 25 may be removed by removing the bolts through flange 30 exposing the upper ends of annular catalyst bed volume 16 between inner tubes 14 and outer tubes 17. New catalyst can be easily charged into the annular catalyst bed space 16 and the upper dome 25 replaced.

Due to unequal thermal expansion of the tube bundles and reactor vessel 26, bellow expansion joint 7 is provided so that neither vessel 26 nor the tubes are stretched or compressed.

The reactor vessel and components of the methanol synthesis reactor may be constructed of any suitable materials known to one skilled in the art and as suitable for temperatures and pressures involved.

While in the foregoing specification this invention has been described in relation to certain preferred embodiments thereof, and many details have been set forth for purpose of illustration. It will be apparent to those skilled in the art that the invention is susceptible to additional embodiments and that certain of the details described herein can be varied considerably without departing from the basic principles of the invention.

We claim:

1. A process for production of methanol comprising:

steam reforming hydrocarbon feedstocks in a tube type reformer wherein reformer furnace burner pressure is maintained at about 100 to about 300 psi and reaction temperature at about 850° to about 1010° C. to form process gas comprising principally $H_2$, CO, $CH_4$, $CO_2$ and $H_2O$;

removing said $CO_2$ from said process gas to an amount of $CO_2$ remaining in said process gas of less than about 500 ppm $CO_2$;

removing said $H_2O$ from said process gas to an amount of $H_2O$ remaining in said process gas of less than about 50 ppm $H_2O$;

adjusting the $H_2/CO$ molar ratio in said process gas to about 2.0 to about 2.5 when necessary;

feeding process gas having a $H_2/CO$ molar ratio of about 2.0 to about 2.5 to a methanol synthesis reactor contacting a methanol forming catalyst not requiring $CO_2$ activation at about 200° to about 300° C. and about 500 to about 800 psi to produce product gas comprising methanol; and recovering liquid methanol having purity greater than about 99.85% pure by cooling said product gas to a temperature below the boiling point of methanol and separating said liquid methanol from gaseous components of said product gas.

2. A process for production of methanol according to claim 1 wherein said process gas is passed from said reformer to said methanol synthesis reactor without passing through a compressor.

3. A process for production of methanol according to claim 2 wherein said catalyst is selected from the group consisting of alkali and alkaline earth promoted copper-chromia catalysts.

4. A process for production of methanol according to claim 3 wherein said catalyst is $Cu-Cr_2O_3$.

5. A process for production of methanol according to claim 4 wherein said $CO_2$ remaining in said process gas is less than about 100 ppm $CO_2$.

6. A process for production of methanol according to claim 5 wherein said $H_2O$ remaining in said process gas is less than about 10 ppm $H_2O$.

7. A process for production of methanol according to claim 6 wherein said burner pressure is maintained at about 150 to about 200 psi.

8. A process for production of methanol according to claim 7 wherein said $H_2/CO$ molar ratio is about 2.0 to about 2.2.

9. A process for production of methanol according to claim 8 wherein said liquid methanol is recovered directly from said product gas solely by said cooling and liquid knock-out separation to recover liquid methanol 10. A process for production of methanol according to claim 9 wherein said reaction temperature of said reformer is about 950° to about 1010° C.

11. A process for production of methanol according to claim 10 wherein said feedstocks comprise natural gas.

12. A process for production of methanol according to claim 1 wherein said catalyst is selected from the group consisting of alkali and alkaline earth promoted copper-chromia catalysts.

13. A process for production of methanol according to claim 1 wherein said catalyst is $Cu-Cr_2O_3$.

14. A process for production of methanol according to claim 1 wherein said $CO_2$ remaining in said process gas is less than about 100 ppm $CO_2$.

15. A process for production of methanol according to claim 1 wherein said $H_2O$ remaining in said process gas is less than about 10 ppm $H_2O$.

16. A process for production of methanol according to claim 1 wherein said burner pressure is maintained at about 150 to about 200 psi.

17. A process for production of methanol according to claim 1 wherein said $H_2/CO$ molar ratio is about 2.0 to about 2.2.

18. A process for production of methanol according to claim 1 wherein said liquid methanol is recovered directly from said product gas solely by said cooling and liquid knock-out separation to recover liquid methanol.

19. A process for production of methanol according to claim 1 wherein said feedstocks comprise natural gas.

20. A process for production of methanol according to claim 1 wherein said reaction temperature of said reformer is about 950° to about 1010° C.

21. In a process for catalytic production of methanol in double tube reactors, the improvement comprising: passing process gas comprising $H_2$ and CO in molar ratio $H_2/CO$ of about 2.0 to about 2.5 through an annular thermal exchange volume between a center plug and an inner tube followed by passing said gas in contact with a catalyst for promotion of reaction of said $H_2$ and CO to product comprising methanol in an annular catalyst bed between said inner tube and an outer tube.

22. In a process for catalytic production of methanol according to claim 21 wherein said reaction is conducted at about 200° to about 300° C. and about 500 to about 800 psi.

23. In a process for catalytic production of methanol according to claim 22 wherein said catalyst does not require $CO_2$ activation.

24. In a process for catalytic production of methanol according to claim 23 wherein said catalyst is selected from the group consisting of alkali and alkaline earth promoted copper-chromia catalysts.

25. In a process for catalytic production of methanol according to claim 24 wherein said catalyst is Cu-$Cr_2O_3$.

26. In a process for catalytic production of methanol according to claim 25 wherein said process gas contains less than about 500 ppm $CO_2$.

27. In a process for catalytic production of methanol according to claim 26 wherein said process gas contains less than about 50 ppm $H_2O$.

28. In a process for catalytic production of methanol according to claim 27 wherein said $H_2/CO$ molar ratio is about 2.0 to about 2.2.

29. In a process for catalytic production of methanol according to claim 28 wherein said methanol is recovered directly from said product solely by said cooling and liquid knock-out separation to recover liquid methanol.

30. In a process for catalytic production of methanol according to claim 29 wherein said annular thermal exchange volume is formed by said center plug having a diameter at least 75 percent the inner diameter of said inner tube.

31. In a process for catalytic production of methanol according to claim 30 wherein said process gas comprises principally $H_2$, CO, $CH_4$, $CO_2$ and $H_2O$ and is produced by steam reforming hydrocarbon feedstocks in a tube type reformer wherein burner pressure is maintained at about 100 to about 300 psi and reformer reaction temperature at about 850° to about 1010° C.

32. In a process for catalytic production of methanol according to claim 31 wherein said reaction temperature of said reformer is about 950° to about 1010° C.

33. In a process for catalytic production of methanol according to claim 32 wherein said feedstocks comprise natural gas.

34. In a process for catalytic production of methanol according to claim 21 wherein said catalyst does not require $CO_2$ activation.

35. In a process for catalytic production of methanol according to claim 21 wherein said catalyst is selected from the group consisting of alkali and alkaline earth promoted copper-chromia catalysts.

36. In a process for catalytic production of methanol according to claim 21 wherein said catalyst is Cu-$Cr_2O_3$.

37. In a process for catalytic production of methanol according to claim 21 wherein said process gas contains less than about 500 ppm $CO_2$.

38. In a process for catalytic production of methanol according to claim 21 wherein said process gas contains less than about 50 ppm $H_2O$.

39. In a process for catalytic production of methanol according to claim 21 wherein said $H_2/CO$ molar ratio is about 2.0 to about 2.2.

40. In a process for catalytic production of methanol according to claim 21 wherein said methanol is recovered directly from said product solely by said cooling and liquid knock-out separation to recover liquid methanol.

41. In a process for catalytic production of methanol according to claim 21 wherein said annular thermal exchange volume is formed by said center plug having a diameter at least 75 percent the inner diameter of said inner tube.

42. In a process for catalytic production of methanol according to claim 21 wherein said process gas comprises principally $H_2$, CO, $CH_4$, $CO_2$ and $H_2O$ and is produced by steam reforming hydrocarbon feedstocks in a tube type reformer wherein burner pressure is maintained at about 100 to about 300 psi and reformer reaction temperature at about 850° to about 1010° C.

43. In a process for catalytic production of methanol according to claim 42 wherein said reaction temperature of said reformer is about 950° to about 1010° C.

44. In a process for catalytic production of methanol according to claim 21 wherein said feedstocks comprise natural gas.

45. In a process for the production of methanol wherein hydrocarbon feedstocks are reformed in a tube type reformer to produce process gas for feeding to a methanol synthesis reactor for catalytic conversion to product gas comprising methanol, the improvement comprising: maintaining reformer furnace burner pressure at about 100 to about 300 psi to maintain reaction temperature at about 850° to about 1010° C. to form said process gas which passes from said reformer to said methanol synthesis reactor without passing through a compressor.

46. In a process according to claim 45 wherein said reformer furnace burner pressure is maintained at about 150 to about 200 psi.

47. In a process according to claim 46 wherein said reaction temperature of said reformer is about 950° to about 1010° C.

* * * * *